US009671361B2

(12) United States Patent
Kim et al.

(10) Patent No.: US 9,671,361 B2
(45) Date of Patent: Jun. 6, 2017

(54) BIOCHIP COMPRISING COVALENTLY IMMOBILIZED BIOACTIVE MOLECULES THROUGH ORGANIC COUPLERS THEREON

(71) Applicant: Kyungpook National University Industry-Academic Cooperation Foundation, Daegu (KR)

(72) Inventors: Youngkyoo Kim, Daegu (KR); Hwajeong Kim, Daegu (KR)

(73) Assignee: Kyungpook National University Industry-Academic Cooperation Foundation (KR)

(*) Notice: Subject to any disclaimer, the term of this patent is extended or adjusted under 35 U.S.C. 154(b) by 449 days.

(21) Appl. No.: 14/447,815

(22) Filed: Jul. 31, 2014

(65) Prior Publication Data
US 2016/0018351 A1  Jan. 21, 2016

(30) Foreign Application Priority Data
Jul. 18, 2014 (KR) ........................ 10-2014-0091229

(51) Int. Cl.
*G01N 27/327* (2006.01)
*C25B 11/04* (2006.01)
*G01N 33/487* (2006.01)

(52) U.S. Cl.
CPC ...... *G01N 27/3277* (2013.01); *C25B 11/0478* (2013.01); *G01N 27/327* (2013.01);
(Continued)

(58) Field of Classification Search
CPC ............. G01N 27/327; G01N 27/3271; G01N 27/3275; G01N 27/22; G01N 27/02;
(Continued)

(56) References Cited

FOREIGN PATENT DOCUMENTS

| EP | 1614694 A1 | * | 1/2006 | ............. C07K 17/14 |
| JP | 05-240825 A | * | 9/1993 | ............. G01N 27/30 |

(Continued)

OTHER PUBLICATIONS

JPO computer-generated English language translation of Fundou et al. JP 05240825 A downloaded Mar. 2, 2017.*

(Continued)

*Primary Examiner* — Alexander Noguerola
(74) *Attorney, Agent, or Firm* — Hovey Williams LLP

(57) ABSTRACT

The present invention relates to a biochip comprising an electrode having a titania coating layer on its surface; an organic coupler comprising two or more carboxylic acid groups and capable of transporting electrons; and bioactive molecules, wherein the organic coupler is covalently bonded to a hydroxyl group of titania on the electrode surface through one carboxylic acid group, and to the bioactive molecules through other one or more carboxylic acid groups, a method for analyzing target molecules using the biochip, a method for diagnosing the development of diseases using the biochip, an electrode provided with a titania coating layer on its surface to which an organic coupler, comprising 2 or more carboxylic acid groups and capable of transporting electrons, is bound, wherein the organic coupler is covalently bonded to a hydroxyl group of titania on the electrode surface through one carboxylic acid group, and a method for preparing the electrode provided with a mesoporous titania coating layer, the method comprising coating a mixed solution of a titania precursor and a template polymer on the top of the electrode, and calcinating the coated electrode under an air flow condition.

20 Claims, 11 Drawing Sheets

(52) U.S. Cl.
CPC ... *G01N 27/3275* (2013.01); *G01N 33/48707* (2013.01); *G01N 2800/28* (2013.01)

(58) Field of Classification Search
CPC .... G01N 27/021; G01N 27/026; G01N 27/04; G01N 27/06; C25B 11/0478
See application file for complete search history.

(56) References Cited

FOREIGN PATENT DOCUMENTS

| KR | 10-0674694 B1 | 1/2007 |
| --- | --- | --- |
| KR | 10-0729147 B1 | 6/2007 |
| KR | 10-2012-0032803 A | 4/2012 |

OTHER PUBLICATIONS

McKenzie et al., "TiO2 phytate films as hosts and conduits for cytochrome c electrochemistry," Bioelectrochemcistry 66 (2005) 41-47.*

Topoglidis et al., Immobilization and Electrochemistry of Negatively Charged Proteins on Modified Nanocrystalline Metal Oxide Electrodes, Electroanalysis 2005, 17, No. 12, pp. 1035-1041.*

Ortel et al., "New Triblock Copolymer Templates, PEO-PB-PEO, for the Synthesis of Titania Films with Controlled Mesopore Size, Wall Thickness, and Bimodal Porosity," Small 2012, vol. 8, No. 2, 298-309.

Kim et al., "Stable Protein Device Platform Based on Pyridine Dicarboxylic Acid-Bound Cubic-Nanostructured Mesoporous Titania Films," ACS Appl. Mater. Interfaces, Jul. 31, 2013, 5, 6873-6878.

* cited by examiner (a) (a-1) Xanthine + $O_2$ + $H_2O$ →[XOD] Uric acid + $O_2^-$ + $H^+$ (a-2) $Cyt\ c^{3+} + O_2^- + H_2O \longrightarrow Cyt\ c^{2+} + O_2$ (a-3) $O_2^- + 2H^+ \longrightarrow O_2 + H_2O$

BIOCHIP COMPRISING COVALENTLY IMMOBILIZED BIOACTIVE MOLECULES THROUGH ORGANIC COUPLERS THEREON

RELATED APPLICATIONS

This application claims priority to Korean Patent Application No. 10-2014-0091229, filed on Jul. 18, 2014, incorporated by reference herein.

FIELD OF THE INVENTION

The present invention relates to a biochip comprising an electrode having a titania coating layer on the surface, an organic coupler comprising 2 or more carboxylic acid groups and capable of transporting electrons, and bioactive molecules; a method for analyzing target molecules using the biochip; a method for diagnosing the development of diseases using the biochip; an electrode provided with a titania coating layer on its surface to which an organic coupler, comprising 2 or more carboxylic acid groups and capable of transporting electrons, is bound; and a method for preparing the electrode provided with a mesoporous titania coating layer, the method comprising coating a mixed solution of a titania precursor and a template polymer on the top of the electrode, and calcinating the coated electrode under air flow.

BACKGROUND OF THE INVENTION

Diagnostic systems such as biosensors have been extensively studied as a result of human desires to overcome diseases and live longer by monitoring the diseases at an early stage. Many commercialized diagnostic systems are based on antigen-antibody immune reactions or ligand-acceptor interactions. However, certain parts of the diseases actually developed in humans may not be detected by such antigen-antibody reactions or ligand-acceptor reactions. In addition, detection systems capable of highly sensitive or quantitative detection are required when detection of micromaterials is needed or quantitation of specific materials, rather than the information on the presence thereof, is needed. The most widely used method for detecting specific biomaterials is labeling a fluorescent material and detecting the fluorescence released therefrom at a specific wavelength. However, such a method of using fluorescence has disadvantages in that 1) a process of labeling a fluorescent substance to a target material is required, and 2) the fluorescent substance exhibits blinking or is quenched in process of time or due to light exposure. Accordingly, as a result of noting that oxidation and reduction are involved in various mechanisms occurring in vivo and that superoxide may act as a main marker for diseases such as cancers, diabetes, Alzheimer's disease or Parkinson's disease, methods of detecting electrochemical signals generated from these processes or from superoxide as a product have emerged as new diagnostic methods.

Cytochrome c (cyt c) is a typical protein capable of detecting superoxide ($O_2^-$) and nitric oxide (NO), and gives signals capable of detecting diseases such as cancers, diabetes, Alzheimer's disease and Parkinson's disease. The most widely used principle in such cyt c-based devices is to monitor electron transfer of cyt c molecules when oxidation and reduction processes for specific interactions with external molecules occur. Accordingly, immobilizing cyt c molecules on an electrode through stable binding is very important in order to acquire reliable signals during interactions, that is, a detection process.

Two most reasonable methods for binding cyt c molecules to an electrode reported to date are (1) binding by coating a mixture of cyt c molecules and a polymeric binder, which is simple and cost-effective, and (2) binding through charge interaction between cyt c molecules and an electrode surface since cyt c molecules have polar functional groups such as amine (—$NH_2$), carboxylic acid (—COOH), and amide bonds (—CONH—). However, these methods only deliver a minimal binding state (for example, physical adhesion), and may not fundamentally render a strong binding force as in covalent bonds.

In view of the above, the inventors of the present invention have carried out extensive research in order to more stably immobilize biomolecules such as protein and DNA (for example, cyt c molecules, a metal-containing heme protein or the like) capable of delivering electrical signals, which are generated in a redox process occurring in vivo, on the surface of an electrode, and as a result, identified that more desirable cyt c molecule immobilization on the surface of an electrode may be accomplished through an anchoring role by covalently bonding the biomolecules using an organic coupler comprising 2 or more carboxylic acid groups, such as pyridine dicarboxylic acid (PDA), as a linker, and completed the present invention (refer to FIG. 1a). In particular, the inventors of the present invention have demonstrated that cyt c molecules may be densely and stably immobilized on the surface of an electrode when a mesoporous titania (titanium dioxide) coating layer is formed on the electrode, since each titania pore may contain 1 or 2 cyt c molecules therein, and covalent bonds with carboxylic acid groups of a PDA coupler may be formed by an esterification reaction using a Ti—OH functional group present abundantly on the titania surface as well.

SUMMARY OF THE INVENTION

An objective of the present invention is to provide a biochip comprising an electrode having a titania coating layer on the surface; an organic coupler comprising 2 or more carboxylic acid groups and capable of transporting electrons; and bioactive molecules, wherein the organic coupler is covalently bonded to a hydroxyl group of titania on the electrode surface through one carboxylic acid group, and to the bioactive molecules through other one or more carboxylic acid groups.

Another objective of the present invention is to provide a method for analyzing target molecules, wherein the target molecules induce the changes in electrochemical signals by the target molecules themselves or products produced by the activity of the target molecules either directly or indirectly binding to or reacting with the bioactive molecules immobilized on the biochip, the method comprising a first step of measuring electrochemical signals of the biochip; a second step of measuring electrochemical signals of the biochip after adding a sample capable of containing target molecules; and a third step of comparing intensities of the electrochemical signals measured before and after the sample addition, which are measured from the first step and the second step.

Another objective of the present invention is to provide a method for diagnosing the development of diseases using the biochip, the method comprising a first step of measuring electrochemical signals of a sample separated from a normal subject using the biochip; a second step of measuring electrochemical signals of a sample separated from a subject with suspected disease using the biochip; and a third step of determining the development of diseases when there is a significant difference between the signals measured from the first step and the signals measured from the second step.

Another objective of the present invention is to provide an electrode provided with a titania coating layer on its surface to which an organic coupler, comprising 2 or more carboxylic acid groups and capable of transporting electrons, is bound, wherein the organic coupler is covalently bonded to a hydroxyl group of titania on the electrode surface through one carboxylic acid group.

Another objective of the present invention is to provide a method for preparing an electrode provided with a mesoporous titania coating layer, the method comprising a first step of coating a mixed solution of a titania precursor and a template polymer on the top of an electrode; and a second step of calcinating the coated electrode under an air flow condition.

In view of the objectives described above, one aspect of the present invention provides a biochip comprising an electrode having a titania (titanium dioxide) coating layer on the surface; an organic coupler comprising 2 or more carboxylic acid groups and capable of transporting electrons; and bioactive molecules, wherein the organic coupler is covalently bonded to a hydroxyl group of titania on the electrode surface through one carboxylic acid group, and to the bioactive molecules through other one or more carboxylic acid groups.

The present invention relates to a biochip for detecting the presence of target molecules and/or activities thereof, and provides a biochip having increased stability and durability by immobilizing bioactive molecules capable of efficiently generating electrochemical signals by either directly or indirectly binding to or reacting with the target molecules or materials produced by the activity of the target molecules on an electrode through covalent bonding. Herein, the covalent bonding is formed through an organic coupler capable of transporting electrons so that the delivery of the generated electrochemical signals is efficiently accomplished.

The titania coating layer may preferably be mesoporous. The titania coating layer may more preferably comprise pores having an average diameter ranging from 5 nm to 10 μm. The titania coating layer may even more preferably comprise pores having an average diameter ranging from 5 nm to 500 nm, but not limited thereto. In addition, an average pore size of the titania coating layer may preferably provide a space capable of capturing one or more bioactive molecules inside the pore, and as many as tens of to hundreds of bioactive molecules may be captured inside one pore and linked.

In specific examples of the present invention, a mesoporous titania coating layer having cubic-type pores with an average diameter of approximately 7 nm is formed on the electrode. Meanwhile, cyt c is bound to titania via pyridine dicarboxylic acid (PDA) as bioactive molecules capable of detecting superoxide. Herein, the cyt c is a protein having an average diameter of approximately 3 nm, and therefore, 1 or 2 cyt c may be located inside each pore of the titania and stably immobilized.

Preferably, the carboxylic acid group of the organic coupler may bind to an amine group of the bioactive molecules either directly or through a linker.

For example, the organic coupler and the bioactive molecules may be bound through a series of reactions using 1-ethyl-3-(3-dimethylaminopropyl) carbodiimide (EDC) as a medium. Specifically, after a free carboxylic acid group is converted to highly reactive 4-(N'-(3-(dimethylamino)propyl)-N-ethylcarbamimidoyloxy)carbonyl by reating with EDC, the carboxylic acid group forms an amide bond with an amine group of cyt c while releasing 1-ethyl-3-(3-dimethylaminopropyl) urea (EDU). The series of reactions described above is for illustrative purposes only, and the scope of the present invention is not limited thereto.

Preferably, the organic coupler comprises 2 or more functional groups for independent and simultaneous binding with titania and bioactive molecules, and may be a molecule having a skeleton capable of transporting electrons. Non-limiting examples of the organic coupler comprise $C_{1-12}$ alkyl; $C_{2-12}$ alkene; $C_{2-12}$ alkyne; polyalkene comprising a plurality of conjugated double bonds; aromatic compounds, which comprise 2 or more carboxylic acid groups; and position isomers (or regioisomers) thereof. More preferably, the organic coupler may be pyridine dicarboxylic acid (PDA), but is not limited thereto.

The bioactive molecules may preferably comprise DNA, RNA or polypeptide.

More preferably, the bioactive molecules may naturally contain metal or be modified to contain metal.

More preferably, the bioactive molecules may be a metal-containing heme protein selected from the group consisting of cytochrome a, cytochrome b, cytochrome c, cytochrome c oxidase, cytochrome P450s, ligninase, peroxidase, hemoglobin, myoglobin, neuroglobin, cytoglobin, leghemoglobin, FixL, CooA, soluble guanylyl cyclase, catalase and endothelial nitric oxide synthase (eNOS), but are not limited thereto. For example, materials capable of 1) covalently bonding to a carboxylic acid group of an organic coupler by inherently comprising an amine group or being modified to have an amine group, 2) sensing electrochemical signals from target molecules, generating electrochemical signals by the interaction with target molecules, or sensing electrochemical signals from products produced by the activity of target molecules, may be used without limit.

Most preferably, the bioactive molecules may be cytochrome c (cyt c). Cytochrome c is a protein belonging to the cytochrome c family, and is a small heme protein loosely bound to the inner membrane of mitochondrion. Cytochrome c is water-soluble and is a main component of an electron transport chain. Cytochrome c may carry out oxidation and reduction reactions, but does not bind to oxygen. The heme group of cytochrome c receives electrons from a bcl complex, that is, a coenzyme Q-cytochrome c reductase complex, and transports the electrons to a cytochrome oxidase complex. In addition, cytochrome c is known to be involved in the initiation of apoptosis. Cytochrome C may function as a catalyst in hydroxylation reactions and oxidation reactions of aromatics, and may exhibit peroxidase activities by the oxidation of various electron donors. In addition, cytochrome c is a protein capable of detecting superoxide or nitrogen monoxide.

Another aspect of the present invention provides a method for analyzing target molecules, wherein the target molecules cause changes in electrochemical signals by the target molecules themselves or products produced by the activity of the target molecules either directly or indirectly binding to or reacting with the bioactive molecules immobilized on the biochip, the method comprising a first step of measuring electrochemical signals of the biochip; a second step of measuring electrochemical signals of the biochip after adding a sample capable of containing target molecules; and a third step of comparing intensities of the electrochemical signals measured before and after the sample addition, which are measured from the first step and the second step.

Preferably, the first step is a step of measuring electrochemical signals from a biochip that does not contain target molecules, and the signals measured therefrom may be regarded as a background signal, and used as a base to estimate the changes shown when adding target molecules thereafter. In other words, the signals measured from the first step are signals exhibited by a substrate, an electrode and coating materials themselves, and by using these as a background signal, more precise detection may be accomplished by distinguishing the signals of these materials from the signals of the sample.

Preferably, the third step may be carried out for the signals obtained in the first step and the second step under the same conditions. The "same conditions" may refer to measuring electrochemical signals under the same voltage and current condition using a solvent or a buffer solution having the same composition, and a biochip having the same condition, except for the sample. As described above, the presence and the degree of changes in the signals measured from the second step are estimated with the signals measured from the first step as a background signal, therefore, analysis accuracy may be improved by identifying conditions other than those of the sample.

Preferably, the presence, the activity or the content of the target molecules, or two or more of these may be measured using the analysis method of the present invention. As described above, the target molecules are a material inducing the changes in electrochemical signals by the target molecules themselves or products produced by the activity of the target molecules either directly or indirectly binding to or reacting with the bioactive molecules immobilized on the biochip of the present invention. Therefore, for samples that does not contain target molecules, the signals measured from the first step and the second step are predicted to be identical. Meanwhile, for samples containing target molecules, the signals measured from the second step may increase or decrease compared to the signals measured from the first step, and the degree thereof may be proportional to the amount of the target molecules present in the sample.

Preferably, the target molecules may comprise superoxide ($O_2^-$), nitrogen monoxide radicals (NO radical), or oxidase or reductase. As described above, bioactive molecules immobilized on a biochip, such as cytochrome c, may directly detect superoxide, nitrogen monoxide radicals or the like. Meanwhile, an oxidase or reductase exhibits activities when a specific substrate corresponding thereto is present, and oxidizing species or reducing species having electrical activities may be produced as the products of the activities. Herein, the produced oxidizing species or reducing species having electrical activities may be sensed by the bioactive molecules.

However, when the target molecule to be analyzed is an oxidase or reductase, the activities of the oxidase or reductase, which is a target molecule, may be induced by additionally adding a substrate corresponding thereto, since the oxidase or reductase exhibits activities when a specific substrate corresponding thereto is present.

In other words, when analyzing an oxidase or reductase as a target molecule, the analysis of the target molecule may be accomplished by detecting electrochemical signals generated due to the reaction between the oxidase or reductase and a substrate corresponding thereto, or signals generated due to active ion species produced from the reaction.

Another aspect of the present invention provides a method for diagnosing the development of diseases using the biochip, the method comprising a first step of measuring electrochemical signals of a sample separated from a normal subject using the biochip; a second step of measuring electrochemical signals of a sample separated from a subject with suspected disease using the biochip; and a third step of determining the development of diseases when there is a significant difference between the signals measured from the first step and the signals measured from the second step.

Preferably, the disease may comprise cancers, diabetes, Alzheimer's disease or Parkinson's disease. In other words, the development of the diseases described above may be diagnosed through electrochemical analysis methods using the biochip of the present invention. However, the disease that may be diagnosed using the information providing method of the present invention is not limited thereto, and all diseases releasing or consuming materials that exhibit electrochemical signals may be included.

Preferably, the electrochemical signals may be generated by active ion species such as superoxide present in the sample. For example, in the diseases, superoxide cumulates due to the impediment of superoxide release or superoxide decomposition, therefore, samples separated from the patients having these diseases, such as blood, urine, sweat or saliva, may contain higher superoxide content than the samples separated from normal individuals.

Another aspect of the present invention provides an electrode provided with a titania coating layer on its surface to which an organic coupler, comprising 2 or more carboxylic acid groups and capable of transporting electrons, is bound, wherein the organic coupler is covalently bonded to a hydroxyl group of titania on the electrode surface through one carboxylic acid group.

Preferably, the organic coupler may bind to bioactive molecules comprising an amine group through one or more free carboxylic acid groups on the other side.

Another aspect of the present invention provides a method for preparing an electrode provided with a mesoporous titania coating layer, the method comprising a first step of coating a mixed solution of a titania precursor and a template polymer on the top of an electrode; and a second step of calcinating the coated electrode under an air flow condition.

Preferably, $TiCl_4$ may be used as the titania precursor, however, the titania precursor is not limited thereto.

Preferably, the template polymer may be a polyethylene oxide-based nonionic multiblock copolymer. Preferably, the template polymer may comprise polyethylene glycol-polypropylene glycol (PEG-PPG), poly-d-(–)(3-hydroxybutyrate)-polyethylene oxide (PHB-PEO), polyisobutylene-polyethylene oxide (PIB-PEO), poly(styrene-b-2-vinylpyridine-b-ethylene oxide (PS-b-P2VP-b-PEO) or the like, but is not limited thereto. More preferably, a polyethylene glycol-polypropylene glycol block copolymer such as Pluronic F-127 may be used as the template polymer, however, the template polymer is not limited thereto. The template polymer forms a certain shape when forming a titania coating layer on an electrode, and may be removed by a calcination process after that, therefore, in order to prepare a titania coating layer having a corresponding shape, the template polymer may be mixed with the titania precursor and used when the coating layer is prepared. For example, by carrying out the process described above using the template polymer, a titania layer having a porous structure such as a mesoporous nano cubic structure may be provided.

Preferably, the second step may be carried out for 1 to 12 hours at 300 to 500° C. The template polymer may be removed through the calcination process. However, the condition of the calcination process is not limited thereto, and may vary depending on the types of the template polymer, the reaction condition and the like, and the condition of the calcination process may be determined by those skilled in the art.

DETAILED DESCRIPTION OF THE EMBODIMENTS

Hereinafter, the present invention will be described in more detail with reference to examples. However, these examples are for illustrative purposes only, and the scope of the present invention is not limited to these examples.

Preparation Example 1: Materials and Preparations

Figure 1:
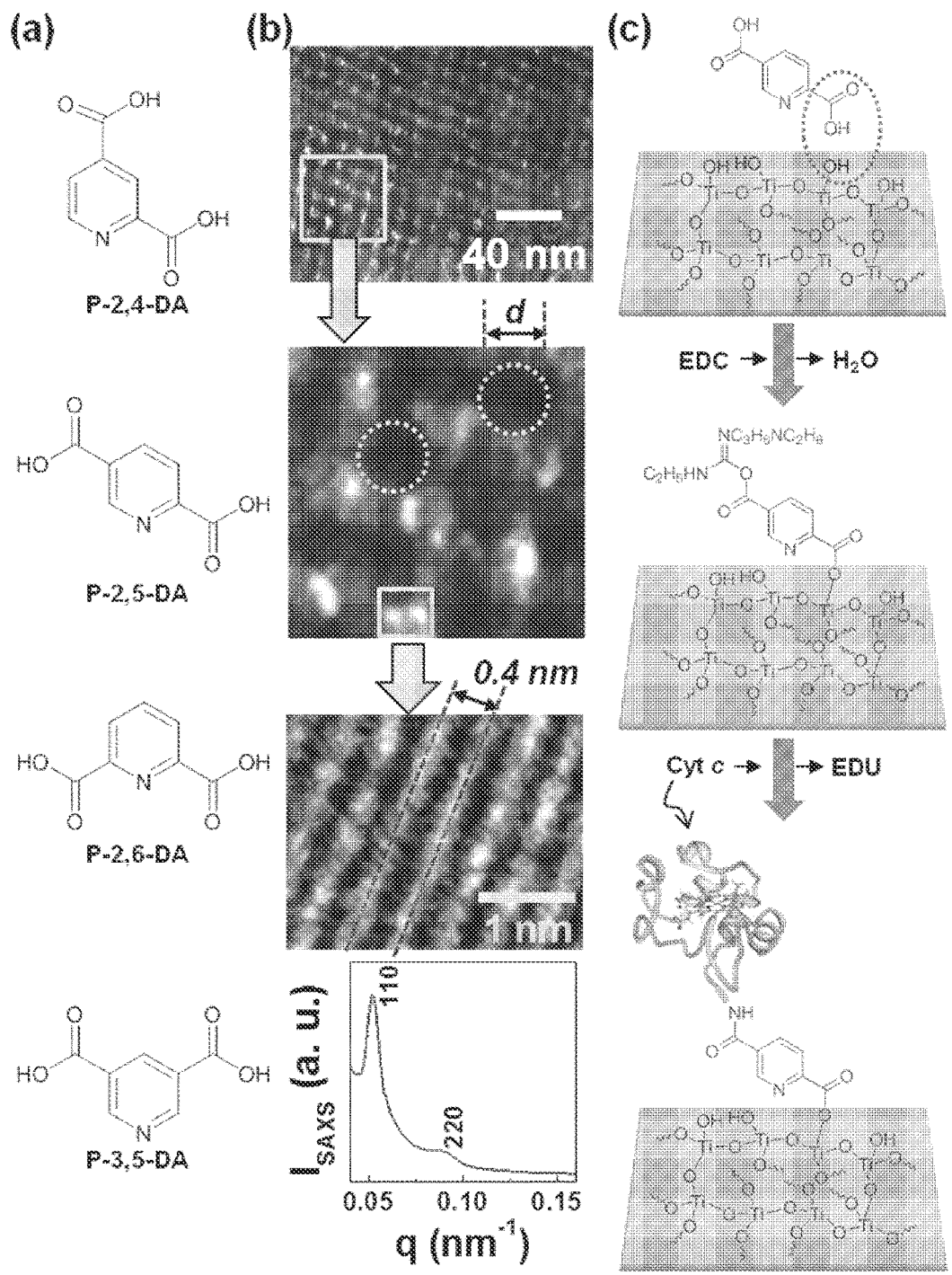
FIG. 1 is a diagram showing chemical structures of PDA, surface conditions of a mesoporous titania (MT) coating layer, and reactions between PDA and MT, and PDA and cyt c according to an exemplary embodiment of the present invention. Specifically, (a) shows chemical structures of PDA (the numbers in the PDA denote the positions of dicarboxylic acids), (b) shows TEM images and a SAXS profile (bottom) of a mesoporous titania film (d=7.3 nm), and (c) shows schematic diagrams for PDA-MT and PDA-cyt c reactions (cyt c size is approximately 3.4 nm).

Prior to coating a mesoporous titania (MT) film, an indium-tin oxide (ITO)-coated glass substrate (10 Ω/m²) was washed with acetone and isopropanol, and dried by nitrogen indraft. A mixed solution (ethanol solvent) of a titania precursor ($TiCl_4$) and a template polymer (Pluronic F-127) was coated on the top of the washed ITO-glass substrate, and the coated substrate was soft-baked for 24 hours at 130° C. Then, a calcination process removing the polymer template was carried out for 5 hours at 450° C. under an air flow condition resulting in the formation of a mesoporous cubic titania nanostructure (FIG. 1b). Then, the sample was washed once more with acetone and isopropanol in order to remove organic impurities remaining during the calcination process. The washed MT-coated ITO-glass substrate was immersed in a solution including PDA molecules (30 mM) as an organic coupler, and 1-ethyl-3-(3-dimethylaminopropyl carbodiimide (EDC, 70 mM) as a medium. An ester reaction between a hydroxyl group (—OH) within the MT and a carboxylic acid group (—COOH) modified with the EDC within the PDA was carried out for 8 hours at 30° C. (FIG. 1c). Then, the PDA-bound MT sample was washed with N,N-dimethylformamide (DMF) in order to remove unreacted PDA molecules and an extra ECD medium. Then, the washed PDA-bound MT-coated ITO-glass substrate was immersed in a cyt c solution (cyt c was dissolved in 5 mM PBS to a concentration of 50 mM: pH 7.4), and an amidation reaction was carried out between a carboxylic acid group (—COOH) modified with the EDC present on the other side of the PDA molecules bound to the MT surface, and an amine group (—NH$_2$) present in the cyt c. The coupling (amidation) reaction was carried out for 4 hours at 25° C. As shown in FIG. 1, the amidation reaction releases 1-ethyl-3-(3-dimethylaminopropyl) urea (EDU). After the amidation reaction, the cyt c-immobilized sample was stored for 24 hours at 4° C. in order to complete the immobilization between the cyt c and the PDA molecules. The cyt c-immobilized sample was washed with 5 mM PBS (pH 7.4) and deionized water in order to remove the cyt c molecules unreacted and physically adhered to the surface of the PDA-bound MT. An electrode coated with a cyt c-immobilized mesoporous titania film was immersed in 0.2 M PBS (pH 7.4) including 0.15 mM xanthine (manufactured by Sigma-Aldrich Co. LLC.) in order to form superoxide ($O_2^-$) molecules when adding 0.15 mM xanthine oxidase (XOD, manufactured by Sigma-Aldrich Co. LLC.), and electrochemical measurements were carried out to identify the applicability as a device for detecting real biomolecules.

Example 1: Measurements

While identifying the nanostructure of the MT film using a high-resolution transmission electron microscopy (HR-TEM, JEM-2010, manufactured by JEOL Ltd.), an average pore size of the MT film was measured using a small-angle X-ray scattering (SAXS) system provided with CuKα (λ=1.608 Å) radiation in the Pohang Accelerator Laboratory (PAL, POSTECH, Korea). The reaction between the PDA (—COOH) and the MT (—OH) through the EDC medium was analyzed using an X-ray photoelectron spectroscopy (XPS, ESCALAB 250, VG Scientifics). Electrochemical properties and superoxide ($O_2^-$) detection of the cyt c-immobilized sample were measured in 0.2 M PBS (pH 7.4) with a scanning rate of 50 mV/s using a potentiostat (263A, manufactured by Princeton Applied Research). The superoxide detection tests were carried out by adding xanthine and xanthine oxidase to the buffer solution. An ITO-coated glass was used as a working electrode, and Ag/AgCl (saturated KCl) and a Pt wire were used as a reference electrode and a counter electrode, respectively. In order to check the stability, cyclic voltammetry (CV) curves were continuously measured up to 240 cycles using the same potentiostat for the cyt c-immobilized electrode installed in 0.2 M PBS (pH 7.4).

As shown in FIG. 1b, a well-organized mesoporous cubic nanostructure (m3m; d-spacing=12.08 nm; unit cell parameter (a)=13.95 nm from the SAXS profile) was measured from the mesoporous titania (MT) film coated on the ITO-glass substrate. The cubic hole size was approximately 7.3 nm, and this shows that the crystal lattices of the titania walls were well aligned with the lattice spacing of 0.4 nm as a measured value. By the esterification reaction using a coupling agent (1-ethyl-3-(3-dimethylaminopropyl) carbodiimide (EDC)), the PDA coupler was covalently bonded to the surface of the MT film, and an amidation reaction of cyt c molecules was carried out with the unreacted carboxylic acid functional group of the PDA molecules bound to the MT film (FIG. 1c). Considering that the molecular size of cyt c molecules is approximately 3.4 nm, 1 or 2 cyt c molecules may be inserted into each cubic hole, and this shows that considerable amounts of cyt c molecules are inserted into the cubic holes of the MT film.

Figure 2:
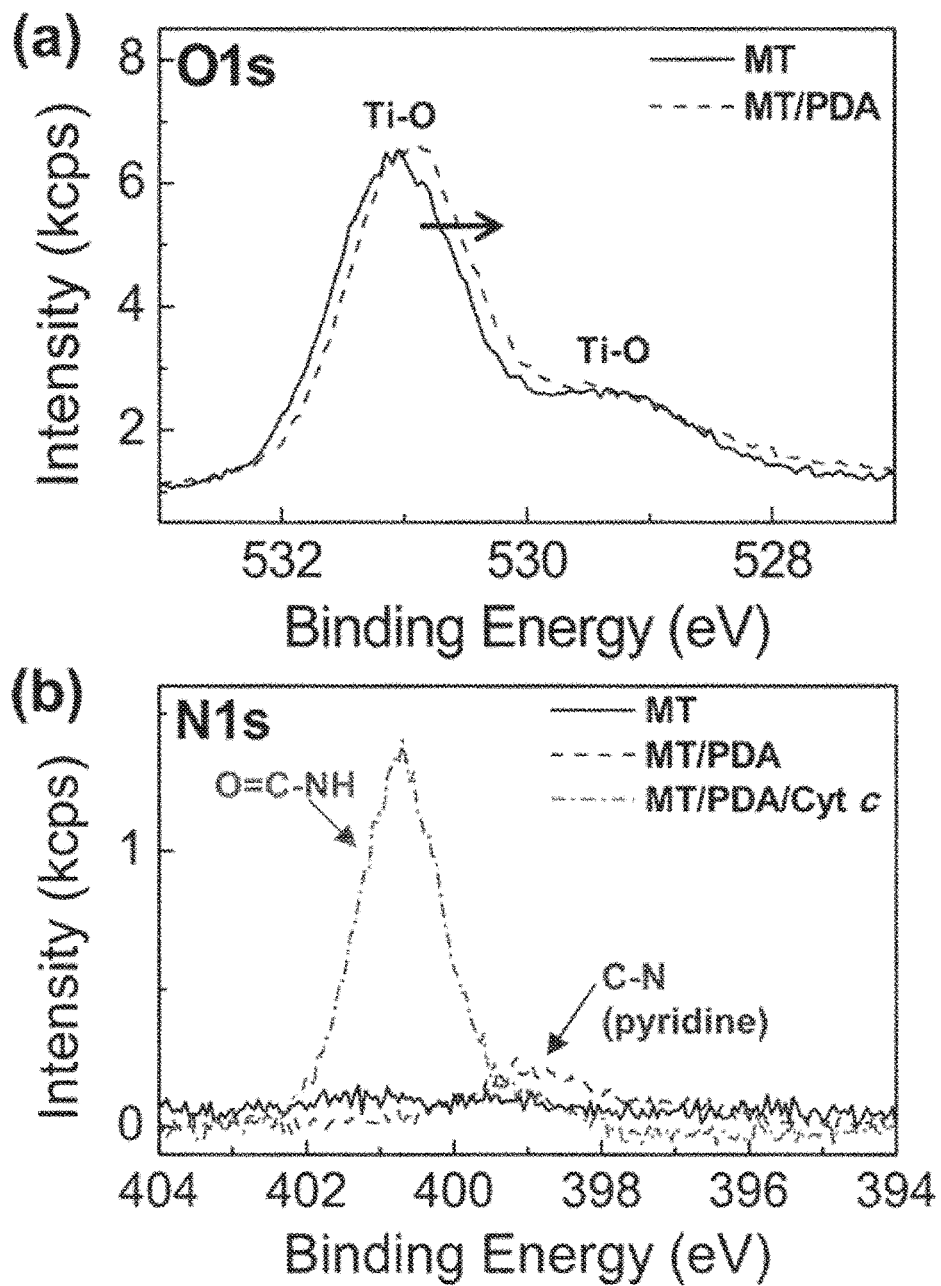
FIG. 2 is a diagram showing O1s and N1s XPS spectra according to an exemplary embodiment of the present invention. (a) shows an O1s XPS spectrum of a mesoporous titania (MT) film and a PDA-bound MT film (MT/PDA) coated on an ITO-glass substrate, and (b) shows an N1s XPS spectrum of an MT film, a PDA-bound MT film and a cyt c-immobilized PDA-bound MT film (MT/PDA/cyt c) coated on an ITO-glass substrate.
Figure 3:
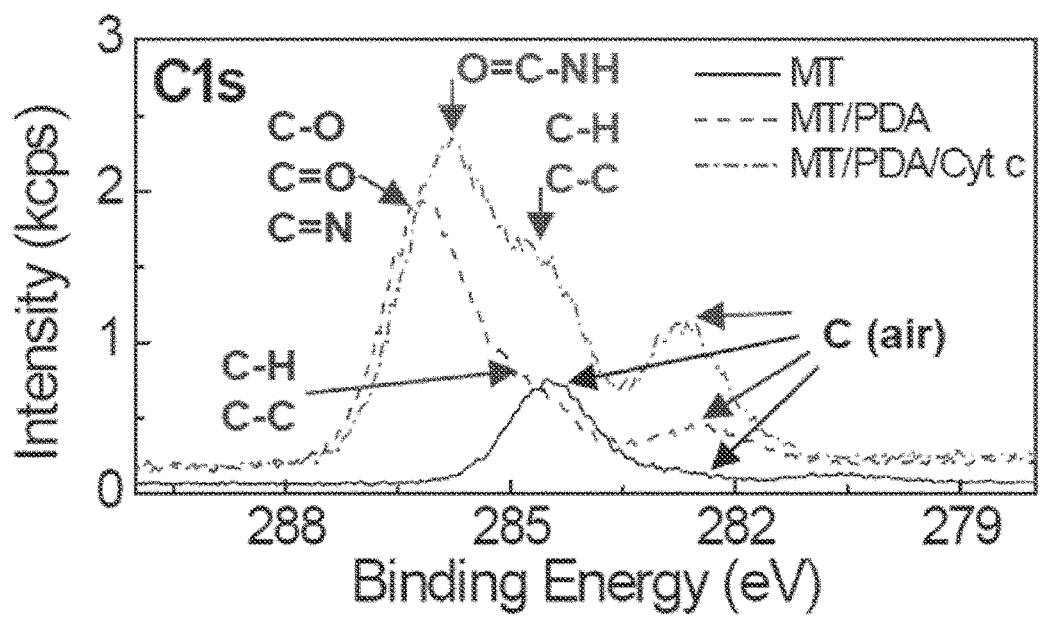
FIG. 3 is a diagram showing a C1s XPS spectrum of an MT film-coated ITO-glass substrate and a PDA-bound MT film (MT/PDA) according to an exemplary embodiment of the present invention.

The esterification reaction of the PDA with respect to the MT surface was identified by the shift of a titania (Ti—O) O1s XPS spectrum toward a lower energy region, which is caused by the reduced polarity due to the presence of an ester functional group (Ti—O—C=O) replacing a Ti—OH functional group (FIG. 2a). This was confirmed from the formation of an N1s XPS peak (C—N bond in a pyridine ring) in the case of the PDA-bound MT film (FIG. 2b). Meanwhile, an amide N1s XPS peak (cyt c) was found at a higher binding energy region with respect to the cyt c-immobilized PDA-bound MT film. In addition, a C1s XPS peak for the reactions of PDA-MT and PDA-cyt c also supported the results described above (FIG. 3).

Figure 4:
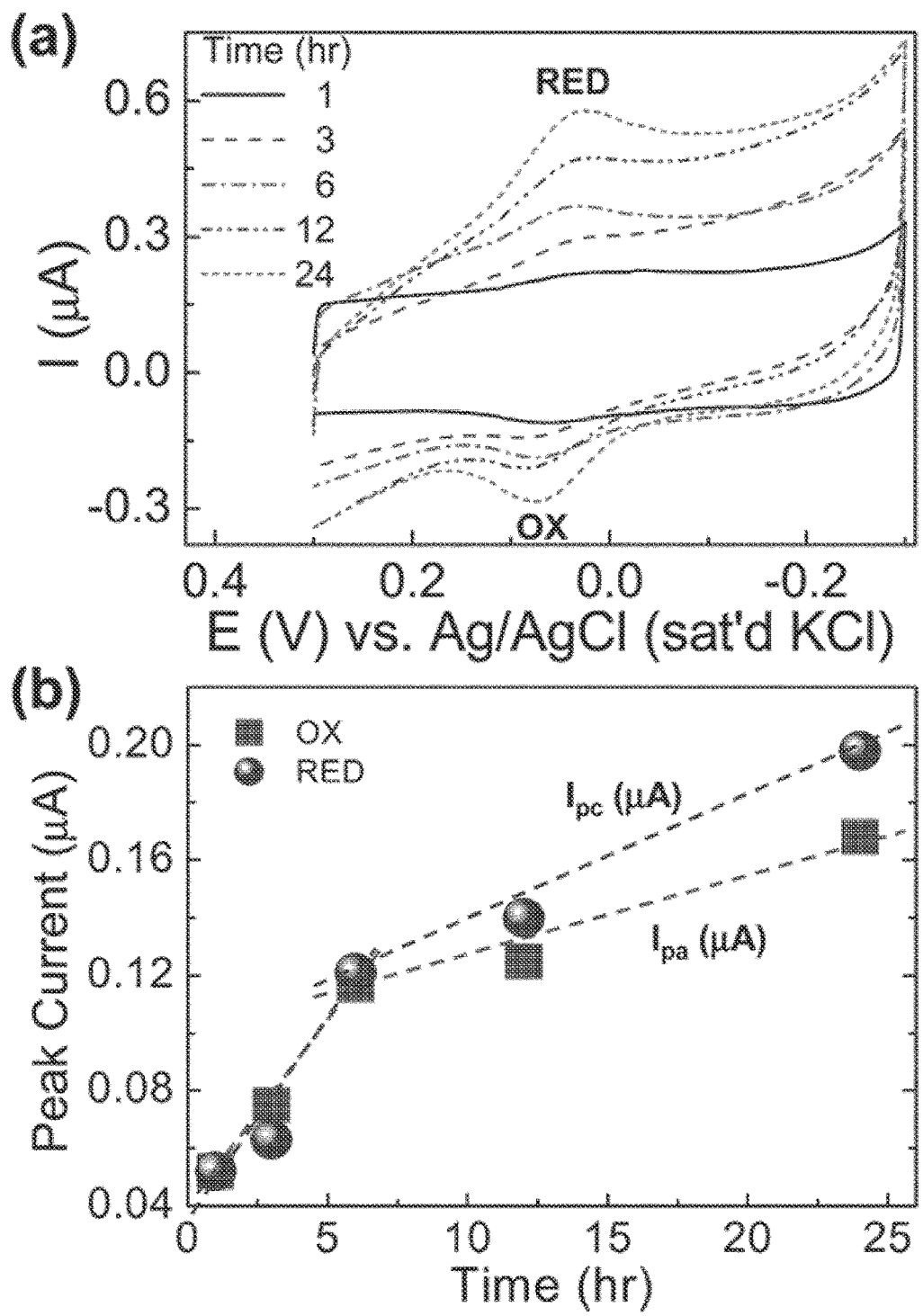
FIG. 4 is a diagram showing (a) a cyclic voltammogram (CV) (OX: oxidation, RED: reduction) according to storage time at 4° C. after initiating a reaction of immobilizing cyt c on a P-2,4-DA-bound MT film (4 hours at 25° C.) in a 5 mM phosphate buffer solution (pH 7.4) including 50 mM cyt c, and (b) oxidation peak current ($I_{pa}$) and reduction peak current ($I_{pc}$) as a function of storage time according to an exemplary embodiment of the present invention. The CV measurement is carried out with a scanning rate of 50 mV/s in a 0.2 M phosphate buffer solution (pH 7.4).

As described in Preparation Example 1, the immobilization reaction of the cyt c with respect to the PDA coupler bound to the MT film was initialized for 4 hours at 25° C., and then completed by reacting for additional 24 hours at 4° C. The additional immobilization time (for example, 24 hours) was determined from a simple experiment while changing the storage time of the PDA-bound MT film sample in a 5 mM phosphate buffer solution (pH 7.4) including 50 mM cyt c at 4° C. Herein, P-2,4-DA was used as the coupler. As shown in FIG. 4a, both reduction and oxidation peaks of cyt c gradually increased in the presence of marginal changes of ΔEp as the storage time increased from 1 hour to 24 hours. Both the oxidation peak current ($I_{pa}$) and the reduction peak current ($I_{pc}$) relatively steeply increased up to 6 hours, and then, exhibited a gentle slope up to 24 hours (FIG. 4b and Table 1).

TABLE 1

| Time (h) | $I_{pa}$ (μA) | $I_{pc}$ (μA) | $E_{pa}$ (mV) | $E_{pc}$ (mV) | $\Delta E_p$ (mV) |
|---|---|---|---|---|---|
| 1 | 0.052 | 0.052 | 68 | 43 | 25 |
| 3 | 0.075 | 0.063 | 79 | 39 | 40 |
| 6 | 0.117 | 0.121 | 71 | 43 | 28 |
| 12 | 0.125 | 0.140 | 79 | 39 | 40 |
| 24 | 0.168 | 0.198 | 71 | 39 | 32 |

The reduction and oxidation peak current measured after storing for 24 hours at 4° C. increased by approximately 280% and approximately 220%, respectively, compared to the values measured after storing for 1 hour. Specifically, as described above, the oxidation and reduction peak current steeply increased up to approximately 6 hours of storage time, and even during the storage time after 6 hours, the oxidation and reduction peak current continuously increased although the degree was somewhat reduced. This shows that cyt c immobilization is progressed quickly for the first 6 hours or so, and then, although somewhat slow, additional cyt c immobilization is progressed. Based on this information, the time for cyt c immobilization was set to 24 hours in order to sufficiently progress the immobilization reaction thereby minimize unreacted organic coupler residues. Moreover, the immobilization time, that is, the storage time during which cyt c was immersed in a solution at 4° C. was employed not to exceed 24 hours, since cyt c deactivation may occur when cyt c was stored for a long time in a solution at 4° C.

Figure 5:
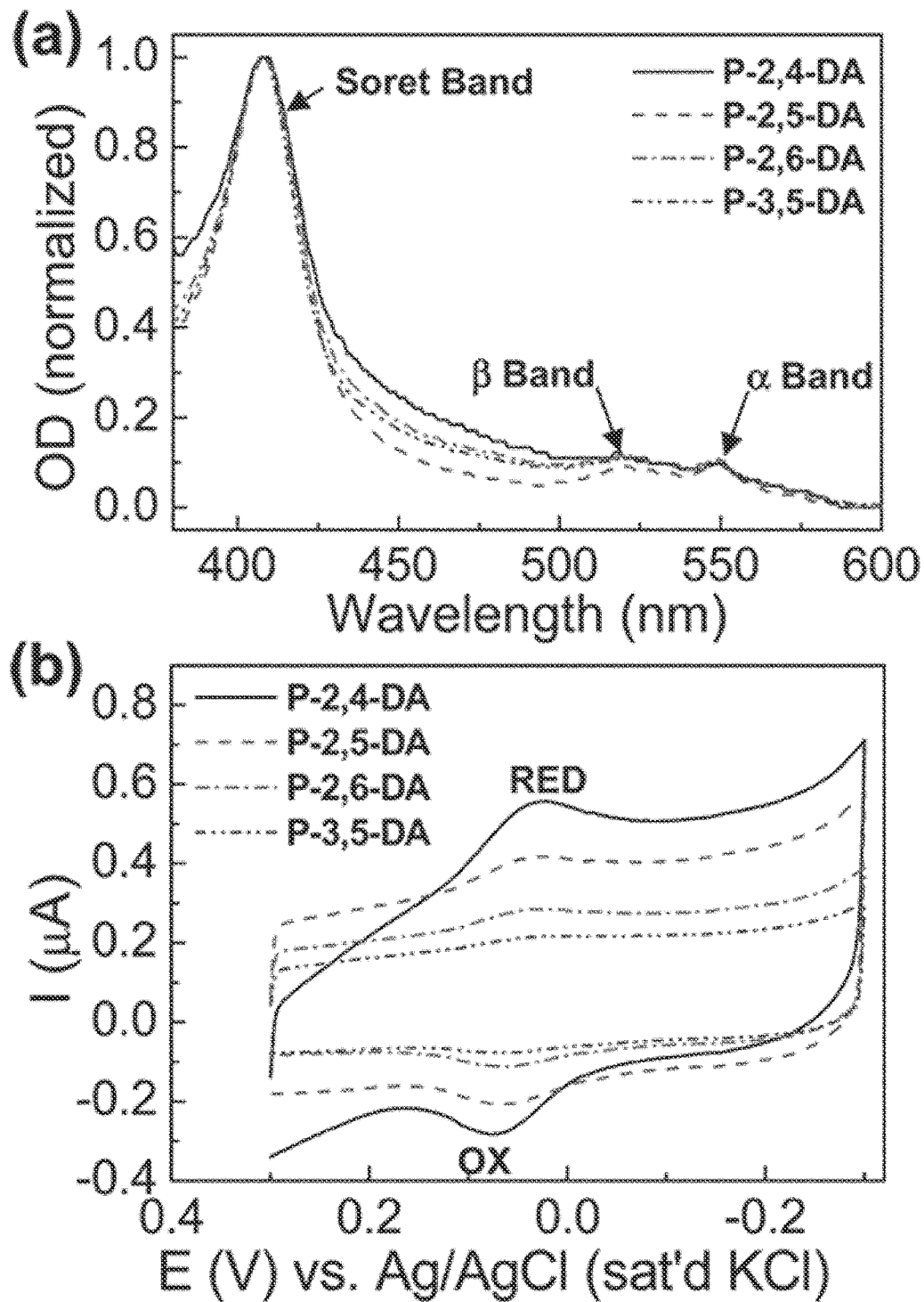
FIG. 5 is a diagram showing (a) an optical absorption spectrum and (b) a cyclic voltammogram (OX: oxidation, RED: reduction) of a cyt c-immobilized PDA-bound MT film with 4 different PDAs according to an exemplary embodiment of the present invention. The CV measurement is carried out with a scanning rate of 50 mV/s in a 0.2 M phosphate buffer solution (pH 7.4).
Figure 6:
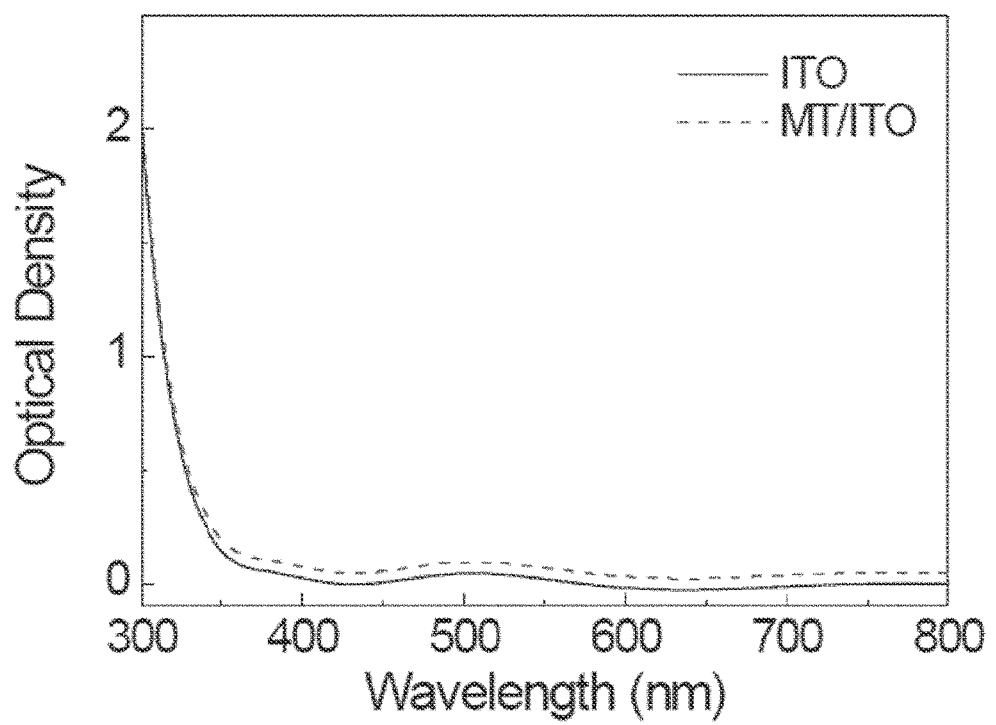
FIG. 6 is a diagram showing an optical absorption spectrum of a noncoated ITO-glass substrate (ITO) and an MT film-coated ITO-glass substrate (ITO/MT) washed after being immersed in identical cyt c solutions for an immobilization reaction between cyt c and a PDA-bound MT sample according to an exemplary embodiment of the present invention.
Figure 7:
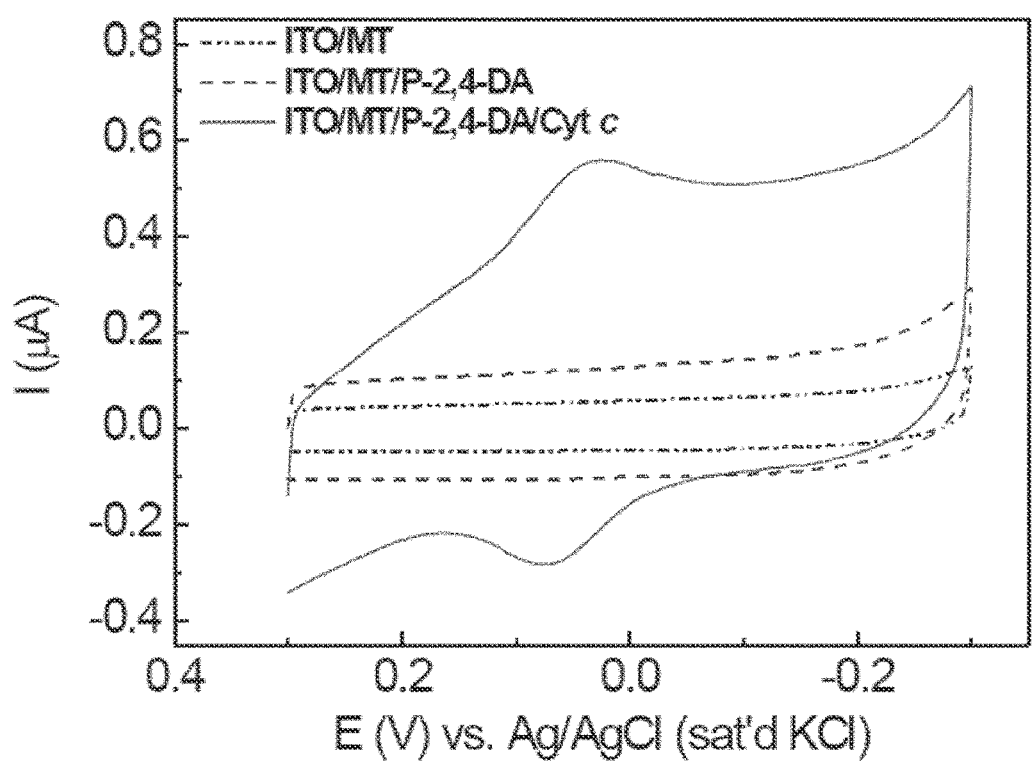
FIG. 7 is a diagram showing cyclic voltammetry curves of ITO/MT, ITO/MT/P-2,4-DA and ITO/MT/P-2,4-DA/cyt c measured with a scanning rate of 50 mV/s in a 0.2 M phosphate buffer solution (pH 7.4) according to an exemplary embodiment of the present invention. The ITO/MT sample and the ITO/MT/P-2,4-DA sample do not show REDOX properties.
Figure 8:
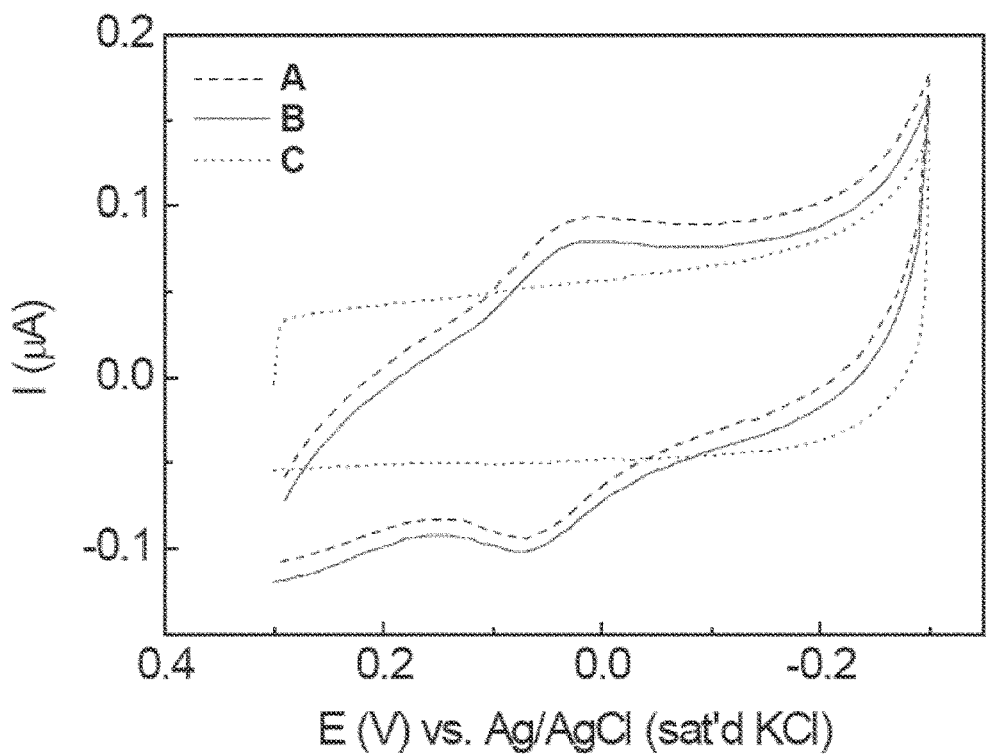
FIG. 8 is a diagram showing cyclic voltammetry curves of a cyt c-immobilized PDA-bound MT film (MT/PDA/cyt c) measured with a scanning rate of 50 mV/s in a 0.2 M phosphate buffer solution (pH 7.4) according to an exemplary embodiment of the present invention. (A) and (B) show curves for an MT/PDA/cyt c film washed with a 5 mM phosphate buffer solution (pH 7.4) and deionized water, and an MT/PDA/cyt c film washed with a 5 mM phosphate buffer solution (pH 7.4) and deionized water after ultrasonic treatment in a 5 mM phosphate buffer solution (pH 7.4) for 5 minutes, respectively, and (C) shows a curve for a PDA-bound MT film washed with a 5 mM phosphate buffer solution (pH 7.4) and deionized water after being immersed in a cyt c solution (dissolved to a concentration of 50 mM in a 5 mM phosphate buffer solution: pH 7.4).

By employing the immobilization condition described above, cyt c immobilization reactions were carried out for all samples prepared with different PDA isomers. As shown in FIG. 5a, these samples showed three characteristic optical absorption peaks of cyt c, such as a Soret band, a β band and an α band. This result indicates that all PDA isomers are capable of including a functional group, that is, a carboxylic acid group, at different positions, or immobilizing a large number of cyt c molecules regardless of the position. A control sample (MT-coated ITO glass substrate) that does not include PDA was prepared by immersing the sample in the identical cyt c solution used for the immobilization reaction between the cyt c and the PDA-bound MT sample, and then washing. No cyt c peaks were observed for the control sample. Meanwhile, the characteristic cyt c absorption peaks were measured when different PDA isomers were used regardless of the types of the PDA isomers (FIG. 6). In particular, considering the cyclic voltammetry (CV) curves of the cyt c-immobilized PDA-bound MT sample (FIG. 5b), the 2,4-positioned PDA isomer (P-2,4-DA) was shown to be more efficient than other isomers in cyt c immobilization (same CV measurement condition was applied for all samples). However, other samples also exhibited noticeable oxidation and reduction peaks, implying that other PDA isomers are also promising potential candidates as a coupler when further optimization is followed. In other words, these results show that molecules having a capability of transporting electrons such as the PDA of the present invention, for example, molecules including aromatic rings capable of electron resonance, may be used as an organic transporter, and also show that more efficient electron transport may be achieved depending on the relative positions of 2 or more carboxylic acid groups, which are functional groups binding to titania and protein, respectively, such as separation distance between the functional groups. The electrochemical parameters obtained from the measurements described above are summarized in Table 2 (FIGS. 7 and 8). A particular attention needs to be paid to the small potential gap between the oxidation and reduction peaks (ΔEp=24 to 32 mV), which indicates that excellent electrochemical reversibility may be provided by the stable cyt c binding through the PDA coupler. Considering the fact that the ΔEp value does not reflect the amount of the immobilized cyt c (relating to the redox peak current intensity), the different ΔEp values according to the use of different PDA isomers may be attributed to different orientations (or positions) of the cyt c molecules due to the chemical structures of the PDA isomers, although further separate studies are required for confirmation.

TABLE 2

| Coupler | $I_{pa}$ (μA) | $I_{pc}$ (μA) | $E_{pa}$ (mV) | $E_{pc}$ (mV) | $\Delta E_p$ (mV) |
| --- | --- | --- | --- | --- | --- |
| P-2,4-DA | 0.198 | 0.168 | 71 | 39 | 32 |
| P-2,5-DA | 0.090 | 0.100 | 64 | 39 | 25 |
| P-2,6-DA | 0.073 | 0.060 | 68 | 39 | 29 |
| P-3,5-DA | 0.079 | 0.082 | 61 | 37 | 24 |

Figure 9:
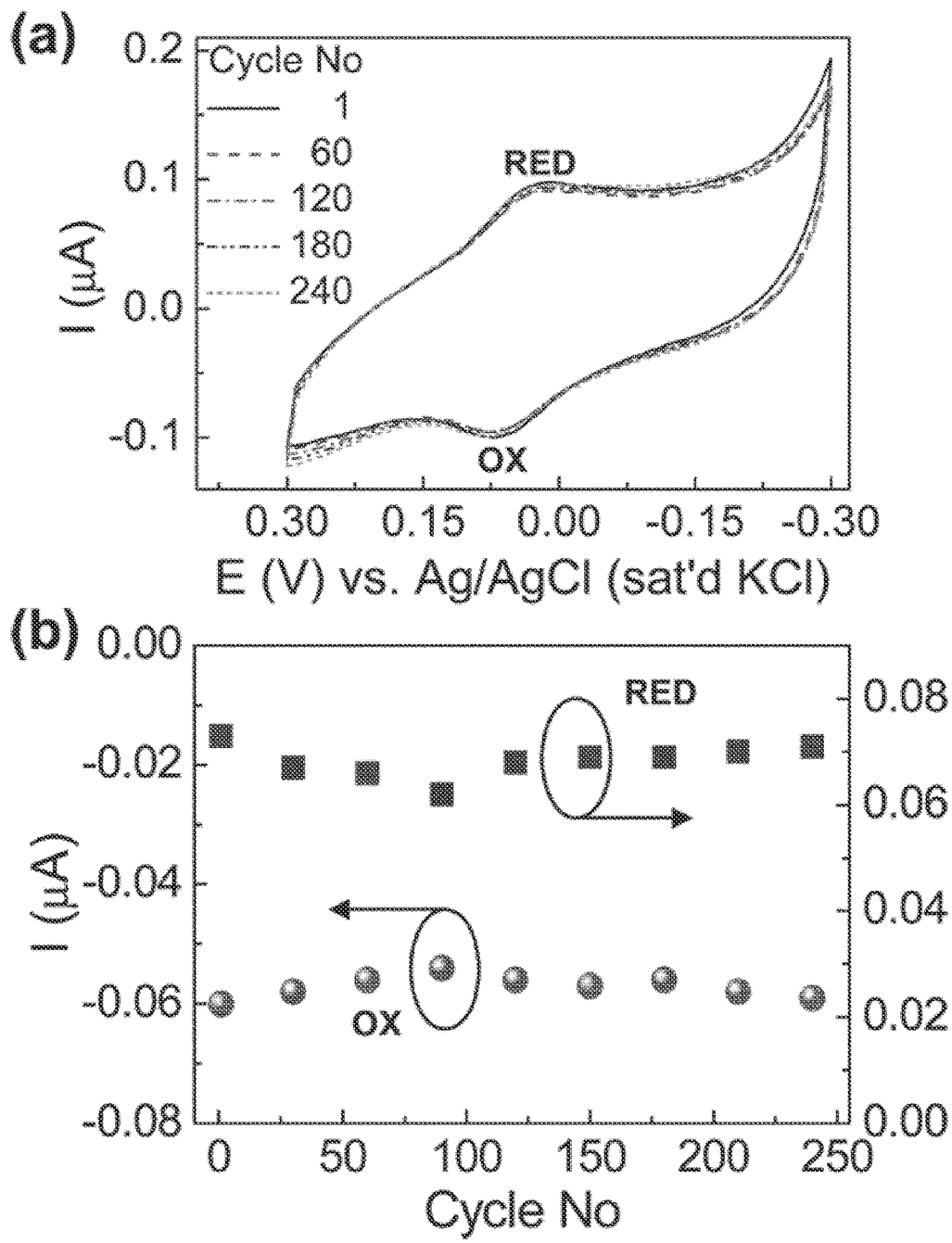
FIG. 9 is a diagram showing (a) a cyclic voltammogram of a cyt c-immobilized PDA-bound MT film (MT/PDA/cyt c) (only 5 curves are shown in order to avoid data confusion), and (b) oxidation (OX) and reduction (RED) peak current intensity variations in the (a) depending on the number of cycles according to an exemplary embodiment of the present invention. The CV measurement is carried out with a scanning rate of 50 mV/s in a 0.2 M phosphate buffer solution (pH 7.4).

In order to examine the stability (durability) of the cyt c-immobilized PDA-bound MT sample of the present invention, CV curves were continuously measured up to 240 cycles. As shown in FIG. 9a, the shape of the CV curves was stably maintained during the whole cycle, although marginal variations were present. For more detailed study, the intensities of the oxidation and reduction current peaks were plotted as a function of cycle numbers. As shown in FIG. 9b, the oxidation peak intensity changed by approximately 10% at 90 cycles, whereas the reduction peak intensity changed by approximately 15% at the same cycle number. After this cycle number, that is, 90 cycles, the peaks were stabilized showing less than 3% variation (1.7% for oxidation and 2.7% for reduction). Such good stability may be attributed mainly to the formation of covalent bonds between the cyt c molecules and the MT surface by the PDA coupler when there are additional effects of nanoholes present on the MT surface capable of strongly immobilizing the cyt c molecules. This result demonstrates that the PDA coupler of the present invention indeed contributes to the stabilized immobilization of cyt c protein, and the PDA-bound MT substrate may be used as a durable platform for detecting and diagnosing biomaterials.

Figure 10:
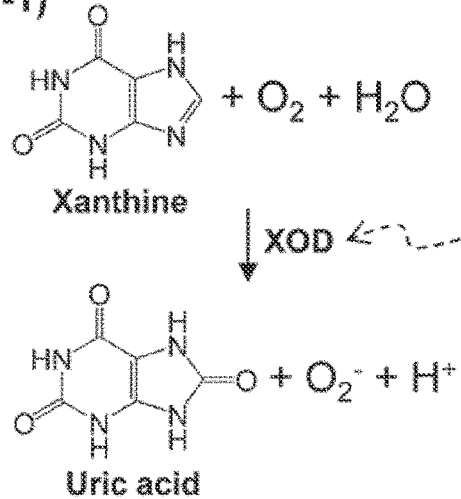
FIG. 10 is a diagram showing (a) production of superoxide ($O_2^-$) in the presence of xanthine and xanthine oxidase (XOD) (a-1) and reactions between cyt c and superoxide (a-2 and a-3), and (b) a cyclic voltammogram for a cyt c-immobilized P-2,4-DA-bound MT film (MT/P-2,4-DA/cyt c) according to an exemplary embodiment of the present invention. Specifically, (b1) shows a measurement result in the absence of xanthine and xanthine oxidase, (b2) shows a measurement result in the presence of xanthine, and (b3) shows a measurement result in the presence of both xanthine and xanthine oxidase (OX; oxidation, RED; reduction). The CV measurement is carried out with a scanning rate of 50 mV/s in a 0.2 M phosphate buffer solution (pH 7.4).
Figure 10:
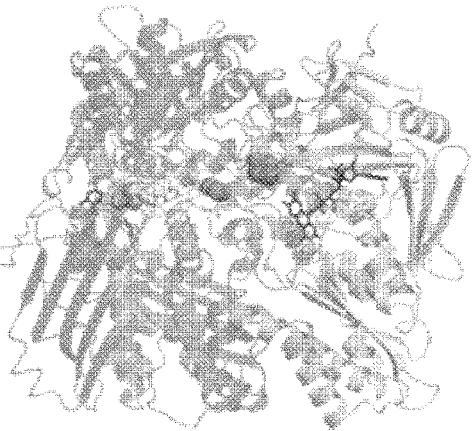
Figure 10:
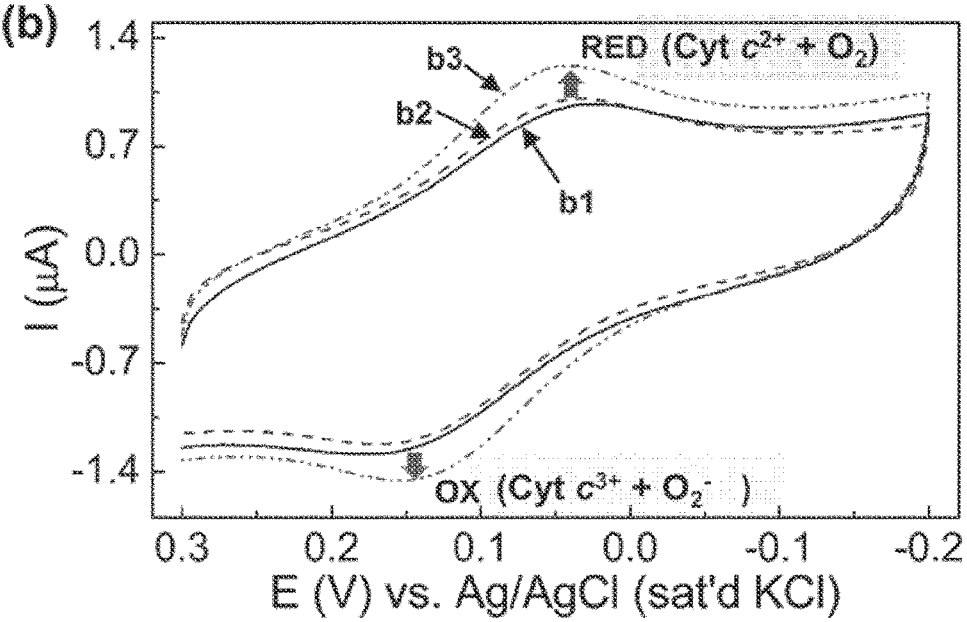
Figure 11:
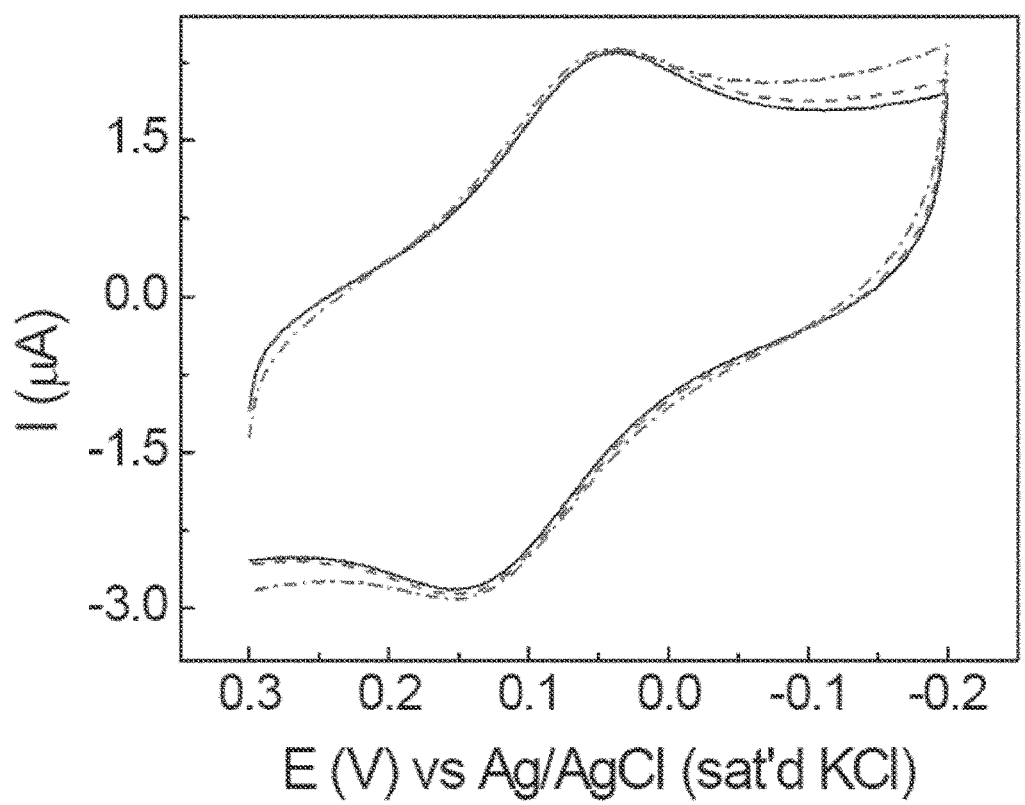
FIG. 11 is a diagram showing a cyclic voltammogram of a cyt c-immobilized P-2,4-DA-bound MT film (MT/P-2,4-DA/cyt c) according to an exemplary embodiment of the present invention. Specifically, the diagram includes cases in which xanthine and xanthine oxidase are not included (black solid line), xanthine is included (green dotted line), and xanthine and xanthine oxidase are all included (red dot-and-dash line). The CV measurement is carried out with a scanning rate of 50 mV/s in a 0.2 M phosphate buffer solution (pH 7.4). Oxygen in the phosphate buffer solution is removed by purging all the solutions with nitrogen gas. In the condition described above, the redox peak current hardly changes, and this shows that superoxide molecules are not produced in aqueous xanthine and xanthine oxidase solutions when oxygen is not present.

Finally, the possibility of application of the cyt c-immobilized PDA-bound MT film of the present invention as a real biomedical device was briefly demonstrated through superoxide ($O_2^-$) detection tests. As shown in FIG. 10a, superoxide molecules were produced by adding xanthine oxidase (XOD) to a buffer solution (0.2 M PBS, pH 7.4) including xanthine molecules in the presence of the cyt c-immobilized PDA-bound MT film. According to the reaction scheme shown in FIG. 10a, pronounced oxidation and reduction current is expected to be formed by the reaction between the produced superoxide molecules and the cyt c-immobilized PDA-bound MT film, and as expected, noticeably increased oxidation and reduction peaks (increased by approximately 35%) were measured in the XOD-added solution, whereas no oxidation and reduction peak changes were observed before the XOD molecule addition (FIG. 10b). As shown in FIG. 11, the redox peaks in the cyt c-immobilized PDA-bound MT film were scarcely changed since superoxide was not produced after removing oxygen molecules by purging with nitrogen gas. This result supports that the cyt c-immobilized PDA-bound MT film of the present invention may be successfully used for detecting superoxide, one of the key indicators for the diagnosis of cancers, diabetes, Alzheimer s disease and Parkinson's disease.

The biochip according to the present invention, which includes an electrode having a mesoporous titania coating layer on the surface, an organic coupler including 2 or more carboxylic acid groups, and bioactive molecules, covalently bonds the bioactive molecules to the titania coated on the electrode surface through the organic coupler, therefore, may provide a stable and highly durable biochip having small signal changes even after long-term storage and repeated use, and in addition to that, may be utilized in qualitative and quantitative analysis of samples, and used for microsample analysis, since the density of bioactive molecules bound to the surface may be adjusted.

What is claimed is:
1. A biochip comprising:
  an electrode having a titania coating layer on its surface;
   an organic coupler comprising 2 or more carboxylic acid groups and capable of transporting electrons; and
  bioactive molecules,
  wherein the organic coupler is covalently bonded to a hydroxyl group of titania on the electrode surface through one carboxylic acid group, and to the bioactive molecules through other one or more carboxylic acid groups.

2. The biochip of claim 1, wherein the titania coating layer is mesoporous.

3. The biochip of claim 2, wherein the titania coating layer comprises pores having an average diameter ranging from 5 nm to 10 µm.

4. The biochip of claim 3, wherein an average pore size of the titania coating layer is capable of capturing one or more bioactive molecules inside the pore.

5. The biochip of claim 1, wherein the carboxylic acid group of the organic coupler binds to an amine group of the bioactive molecules either directly or through a linker.

6. The biochip of claim 1, wherein the organic coupler is selected from the group consisting of $C_{1-12}$ alkyl; $C_{2-12}$ alkene; $C_{2-12}$ alkyne; polyalkene comprising a plurality of conjugated double bonds; aromatic compounds, which comprise 2 or more carboxylic acid groups; and position isomers (or regioisomers) thereof.

7. The biochip of claim 6, wherein the organic coupler is pyridine dicarboxylic acid (PDA).

8. The biochip of claim 1, wherein the bioactive molecules are DNA, RNA or polypeptide.

9. The biochip of claim 8, wherein the bioactive molecules naturally contain metal or are modified to contain metal.

10. The biochip of claim 9, wherein the bioactive molecules are a metal-containing heme protein selected from the group consisting of cytochrome a, cytochrome b, cytochrome c, cytochrome c oxidase, cytochrome P450s, ligninase, peroxidase, hemoglobin, myoglobin, neuroglobin, cytoglobin, leghemoglobin, FixL, CooA, soluble guanylyl cyclase, catalase and endothelial nitric oxide synthase (eNOS).

11. A method for analyzing target molecules, wherein the target molecules induce changes in electrochemical signals by the target molecules themselves or products produced by the activity of the target molecules either directly or indirectly binding to or reacting with bioactive molecules immobilized on the biochip of claim 1, the method comprising:
   a first step of measuring electrochemical signals of the biochip of claim 1;
   a second step of measuring electrochemical signals of the biochip after adding a sample capable of containing target molecules; and
   a third step of comparing intensities of the electrochemical signals measured before and after the sample addition, which are measured from the first step and the second step.

12. The analysis method of claim 11, which measures a presence, an activity or a content of the target molecules, or two or more of these.

13. The analysis method of claim 11, wherein the target molecules are superoxide ($O_2^-$), nitrogen monoxide radicals (NO radicals), or oxidase or reductase.

14. The analysis method of claim 13, wherein, when the target molecules are oxidase or reductase, a substrate corresponding to the same is further added.

15. The analysis method of claim 14, which detects electrochemical signals generated due to a reaction between the oxidase or reductase, and the substrate corresponding thereto, or signals generated due to active ion species produced from the reaction.

16. A method for diagnosing the development of diseases comprising:
   a first step of measuring electrochemical signals of a sample separated from a normal subject using the biochip of claim 1;
   a second step of measuring electrochemical signals of a sample separated from a subject with a suspected disease using the biochip; and
   a third step of determining the development of diseases when there is a significant difference between the signals measured from the first step and those measured from the second step.

17. The method for diagnosing of claim 16, wherein the disease is a cancer, diabetes, Alzheimer's disease or Parkinson's disease.

18. The method for diagnosing of claim 16, wherein the electrochemical signals are generated by superoxide in the sample.

19. An electrode provided with a titania coating layer on its surface to which an organic coupler, comprising 2 or more carboxylic acid groups and capable of transporting electrons, is bound, wherein the organic coupler is covalently bonded to a hydroxyl group of titania on the electrode surface through one carboxylic acid group.

20. The electrode of claim 19, wherein the organic coupler binds to bioactive molecules comprising an amine group through one or more free carboxylic acid groups on the other side.

* * * * *